United States Patent
Mogensen et al.

(10) Patent No.: US 11,628,056 B2
(45) Date of Patent: Apr. 18, 2023

(54) GRAFT FOR TREATING THE DISTAL AORTIC ARCH AND DESCENDING AORTA IN TYPE A PATIENTS

(71) Applicant: Cook Medical Technologies LLC, Bloomington, IN (US)

(72) Inventors: John Mogensen, Hvidovre (DE); François Dagenais, Québec (CA)

(73) Assignee: Cook Medical Technologies LLC, Bloomington, IN (US)

( * ) Notice: Subject to any disclaimer, the term of this patent is extended or adjusted under 35 U.S.C. 154(b) by 500 days.

(21) Appl. No.: 15/820,896

(22) Filed: Nov. 22, 2017

(65) Prior Publication Data
US 2019/0151071 A1  May 23, 2019

(51) Int. Cl.
| | |
|---|---|
| A61F 2/07 | (2013.01) |
| A61F 2/954 | (2013.01) |
| A61F 2/97 | (2013.01) |
| A61F 2/844 | (2013.01) |

(52) U.S. Cl.
CPC ............. *A61F 2/07* (2013.01); *A61F 2/954* (2013.01); *A61F 2/97* (2013.01); *A61F 2/844* (2013.01); *A61F 2002/075* (2013.01); *A61F 2220/0075* (2013.01); *A61F 2250/0098* (2013.01)

(58) Field of Classification Search
CPC ............. A61F 2/82; A61F 2/07; A61F 2/954
See application file for complete search history.

(56) References Cited

U.S. PATENT DOCUMENTS

| | | |
|---|---|---|
| 4,214,587 A | 7/1980 | Sakura |
| 4,733,664 A | 3/1988 | Kirsch et al. |
| 4,922,905 A | 5/1990 | Strecker |
| 5,653,743 A | 8/1997 | Martin |
| 5,702,419 A | 12/1997 | Berry et al. |
| 5,709,713 A | 1/1998 | Evans et al. |
| 6,102,938 A | 8/2000 | Evans et al. |

(Continued)

FOREIGN PATENT DOCUMENTS

| | | |
|---|---|---|
| CA | 2740831 A1 | 4/2010 |
| EP | 1336393 A2 | 8/2003 |

(Continued)

OTHER PUBLICATIONS

European Extended Search Report, Appl. #17275181.0, Cook Medical Technologies LLC, dated Apr. 16, 2018.

(Continued)

*Primary Examiner* — Matthew W Schall
(74) *Attorney, Agent, or Firm* — Crowell & Moring LLP (57) ABSTRACT

A prosthetic graft assembly (40, 120) is disclosed for placement of a patient's aortic arch and repair of the descending aorta in a procedure which requires only a sternotomy. The assembly includes a descending graft element (40) which includes an eversible cuff (52) which can be wrapped over a cut end (26) of the descending aorta (18). Distal perfusion can be re-established prior to aortic arch replacement. A second prosthetic element (120), optimised to the patient, is fitted with a replacement for the aortic arch and attached to the descending aorta graft (40). An introducer assembly (30) having a transparent or translucent sheath (70) enables the descending aortic graft element (40) to be deployed without the use of x-rays.

20 Claims, 11 Drawing Sheets

(56) References Cited

U.S. PATENT DOCUMENTS

| | | | |
|---|---|---|---|
| 6,305,436 | B1 | 10/2001 | Andersen et al. |
| 6,767,358 | B2 | 7/2004 | Leonhardt et al. |
| 7,488,344 | B2 | 2/2009 | Hartley et al. |
| 7,493,154 | B2 | 2/2009 | Bonner et al. |
| 8,038,710 | B2 | 10/2011 | Fearnot et al. |
| 8,092,511 | B2 | 1/2012 | Chuter |
| 8,133,266 | B2 | 3/2012 | Thomas et al. |
| 8,480,726 | B2 | 7/2013 | Cunningham et al. |
| 8,906,086 | B2 | 12/2014 | Roeder et al. |
| 8,992,608 | B2 | 3/2015 | Haug et al. |
| 2004/0117004 | A1 | 6/2004 | Osborne et al. |
| 2006/0276883 | A1 | 12/2006 | Greenberg et al. |
| 2008/0255652 | A1 | 10/2008 | Thomas et al. |
| 2009/0076587 | A1* | 3/2009 | Cully ............... A61F 2/82 623/1.13 |
| 2012/0071960 | A1 | 3/2012 | Tani |
| 2012/0116496 | A1 | 5/2012 | Chuter et al. |
| 2016/0158045 | A1 | 6/2016 | Havel et al. |

FOREIGN PATENT DOCUMENTS

| | | |
|---|---|---|
| EP | 1245202 B1 | 8/2004 |
| EP | 1736116 B1 | 11/2009 |
| WO | 2006124822 A1 | 11/2006 |
| WO | WO 2006-124822 A1 | 11/2006 |
| WO | 2009035679 A1 | 3/2009 |
| WO | WO 2009-035679 A1 | 3/2009 |
| WO | 2009145901 A1 | 12/2009 |
| WO | WO 2009-145901 A1 | 12/2009 |
| WO | 2013060740 A1 | 5/2013 |
| WO | WO 2013-060740 A1 | 5/2013 |

OTHER PUBLICATIONS

European Extended Search Report, Application No. 17275181.0, Cook Medical Technologies LLC, dated Apr. 16, 2018.
European Journal of Cardio-Thoracic Surgery, vol. 43, Malakh Shrestha et al, "Total Aortic Arch Replacement with a Novel Four-Branched Frozen Elephant Trunk Graft: First-in-man results", p. 406-410, May 31, 2012.
The Annals of Thoracic Surgery, vol. 83, Hassina Baraki et al, "The Frozen Elephant Trunk Technique for Treatment of Thoracic Aortic Aneurysms" p. 819-823, 2007.
The Journal of Thoracic and Cardiovascular Surgery, vol. 125, No. 6, Matthias Karck et al, "The Frozen Elephant Trunk Technique: A New Treatment for Thoracic Aortic Aneurysms", Jun. 2003.
UK Search and Examination Report, Cook Medical Technologies LLC, dated Mar. 31, 2017.
Malakh Shrestha, et al, "Total Aortic Arch Replacement with a Novel Four-Branched Frozen Elephant Trunk Graft: First-in-Man Results", European Journal of Cardio-Thoracic Surgery, May 31, 2012, p. 406-410, vol. 43.
Hassina Baraki, et al, "The Frozen Elephant Trunk Technique for Treatment of Thoracic Aortic Aneurysms", The Annals of Thoracic Surgery, 2007, p. 819-823, vol. 83.
Matthias Karck, et al, "The Frozen Elephant Trunk Technique: A New Treatment for Thoracic Aortic Aneurysms", The Journal of Thoracic and Cardiovascular Surgery, Jun. 2003, p. 1550-1553, vol. 125, No. 6.

* cited by examiner

GRAFT FOR TREATING THE DISTAL AORTIC ARCH AND DESCENDING AORTA IN TYPE A PATIENTS

CROSS REFERENCE TO RELATED APPLICATIONS

This application claims the benefit of U.S. provisional application, Ser. No. 62/425,368 filed on Nov. 22, 2016, entitled "Graft for Treating the Distal Aortic Arch and Descending Aorta in Type A Patients" the entire contents of which are incorporated herein by reference.

TECHNICAL FIELD

The present invention relates to a graft assembly for the treatment of the descending aorta in patients, particularly Type A patients in which prosthetic replacement of the aortic arch and, in some instances, the descending aorta is required. The preferred embodiments disclosed herein provide a hybrid assembly with an antegrade graft for treating the distal aortic arch and descending aorta and a second graft element for treating the aortic arch and ascending aorta.

BACKGROUND OF THE INVENTION

Surgical treatment of type A patients is complicated and is still associated with high morbidity and mortality rates. The orientation of the aorta means that surgery has to be carried out in two locations on the patient. Replacement of the ascending aorta and the aortic arch can be effected by a median sternotomy. This is generally a successful procedure as a sternotomy is a relatively pain free process given the lack of muscular tissue in that region of the chest. Replacement of the descending aorta requires the patient to be turned onto the side and then a second access point used, which involves the opening of a side of the chest cavity, by breaking the patient's ribs and collapsing the lung. Overall, this procedure is painful and traumatic, with at best long convalescence periods and with elevated risk of morbidity and mortality.

Attempts have been made at developing a prosthesis which avoid the need to made the second aperture, by cutting the descending aorta transversally just distal to the arch and implanting into the descending aorta a stent graft from the side of the sternotomy. The stent graft includes also aortic arch and ascending aorta graft sections, with branches for the carotid and subclavian arteries. While this can significantly improve surgery times, patient healing and complications, differing surgical and patient means it is difficult to make a prosthetic device which is suitable for all. While some devices may be configurable in situ, this adds surgical complication and extends surgery time.

More specifically, stent-grafts were initially designed to be used during type A (DeBakey type 1) dissections. Possible indications for type A aortic dissections include:

(i) extensive arch tear or proximal descending aortic tear in which the graft will facilitate the repair;

(ii) presence of severe dynamic malperfusion (distal arch aortic occlusion);

(iii) secure distal anastomosis hemostasis;

(iv) enhance false lumen thrombosis and decrease late aneurysmal degeneration of the descending aorta, reported in up to 30% of patients after DeBakey type 1 repair.

In addition to type A repair, a graft may be used in patients with distal arch/proximal descending aneurysms or patients with chronic dissected aneurysms following type A repair.

There are reports, mainly from Asian centres, of the usage of tailor made hybrid devices. The incidence of false lumen thrombosis of the descending aorta is reported in up to 80-90% of patients compared to an incidence of less than 10% in patients without a hybrid stent-graft inserted in the descending aorta. Furthermore these extensive procedures may be performed with results comparable to a standard procedure without placement of a hybrid graft. A major drawback of an extended procedure is a rate of paraplegia in 3-7% of patients, a complication which is not reported with procedures without a stent-graft. The risk of paraplegia is mainly related to the extended period of non-perfusion of the distal body owing to the complex arch reconstruction.

One known device incorporates a four branch graft to the stent. Deployment is complex and arch vessel branch orientation is often difficult. The distal anastomosis is performed using a collar on the graft. Positioning of this collar may be difficult, rendering the distal anastomosis tedious. Distal perfusion during distal anastomosis is impossible. Another known device has a configuration without branches. A collar is used for the distal anastomosis with the same limitations as the branched device. Distal perfusion is also impossible while performing the distal anastomosis.

These limitations of known procedures and devices lead to high risk of medical complications.

Some examples of prosthetic devices for such uses are disclosed in U.S. Pat. Nos. 5,653,743, 6,767,358, 8,092,511, 8,133,266, WO-2009/145901, EP-1,736,116 and in "Total aortic arch replacement with a novel four-branched frozen elephant trunk graft: first-in-man results" by Malakh Shrestha et al in European Journal of Cardio-Thoracic Surgery 43 (2013) 406-410.

SUMMARY OF THE INVENTION

The present invention seeks to provide an improved implantable medical device and method of treating aortic diseases particularly in Type A patients.

According to an aspect of the present invention, there is provided a graft assembly including a unitary tubular graft element having a length, a first end, a second end and an axis; a plurality of stent elements extending along a majority of the length of the tubular graft element from the first end thereof, to provide a stented first portion of the tubular graft element; the tubular element from an end of the first stented portion to the second end being free of stents and forming a non-stented second portion of the tubular graft element; wherein the second portion is a minor portion of the length of the tubular graft element; the second portion having a circumference at least large as a circumference of the first portion so as to be eversible over the first portion for form a coaxially overlapping cuff to the tubular graft.

The graft assembly can be deployed in the descending aorta, with the cuff everted over the severed end of the descending aorta, so as to provide a prosthetic replacement to the diseased descending aorta and a fixation point for a second prosthetic element for the repair of the aortic arch and ascending aorta. The graft assembly has a form which is readily deployable without needing to make a second entry point into the patient.

The assembly taught herein is particularly suited for the treatment of type A dissections and/or thoracic aneurysms where the aneurysm extends through the aortic arch and the descending aorta.

Preferably, the second portion of the tubular graft element has a length of 20 to 40 millimetres, most preferably of around 30 to 32 millimetres. This length enables the cuff to cover the thickness and a sufficient length of the outside of the descending aorta to provide a solid fixation not only of the stented portion of the graft assembly but also for a second prosthetic element.

In an embodiment, the first portion of the tubular graft element has a length of around 10 to 20 centimetres, for instance of around 15 centimetres. The skilled person will appreciate that the length of stent graft in the descending aorta will depend on the length of diseased vessel and the patient's anatomy.

The tubular graft element advantageously has a single lumen. In other words, the tubular graft element is a single tubular element such that the first and second portions are part of the same tube and preferably linearly coaxial with one another. The tubular graft element preferably has a substantially cylindrical form. In other words, the tubular graft element preferably has a uniform open diameter throughout its length, that is substantially the same open diameter.

In other embodiments, the tubular graft element may have different diameters along its length, for instance to taper and/or to have a larger diameter portion at the unstented (that is, stent free) part of the assembly. The stented portion can be tapered to have a smaller diameter distal.

In practical embodiments the tubular graft element is formed of polyethylene terephthalate (PET), polytetrafluoroethylene (PTFE), polyester (for instance Dacron).

The stent elements may be formed of Nitinol, stainless steel or other suitable materials known in the art.

The graft assembly is advantageously designed for use in the treatment of the descending aorta, wherein the second portion of the tubular graft element is eversible over the transversally severed aorta wall. In this embodiment, a second graft element is preferably sutured to the tubular graft element, wherein the second graft element is formed to fit to the aortic arch of a patient.

The provision of two separate graft elements means that an aortic arch section can be provided specifically for that patient's condition and anatomy, which can significantly speed up the surgical process and provide a prosthetic replacement much better suited to that patient. Increased speed and the possibility of re-establishing perfusion into the descending aorta during the procedure can significantly reduce or eliminate the risk of medical complications caused by the procedure. Moreover, it is possible to re-establish distal perfusion once the thoracic prosthesis (the descending aortic arch graft section) has been deployed and during the arch replacement.

Providing the possibility to perfuse within the stent-graft during circulatory arrest can minimize distal ischemia including to the spinal cord, decreasing or eliminating the risk of paraplegia. The preferred embodiments provide the following additional advantages:

(i) a short and easy pusher rod deployment system;

(ii) a transparent or translucent sheath which allows controlled and precise graft deployment;

(iii) a proximal un-stented graft portion which can be easily tailored to the aortic arch wall;

(iv) since the graft is terminated at the level of the transected arch, an endotracheal tube may be inserted and inflated within the hybrid stent allowing for distal body perfusion. This may be done before and during the distal anastomosis.

These advantages can have significant clinical impact. The easy and reliable deployment system may be adapted to many clinical situations in addition to type A dissections, such as distal arch aneurysms and chronic dissection cases.

The possibility to initiate distal perfusion has significant benefits. First, this ensures distal body perfusion including spinal cord perfusion. Paraplegia risk can be significantly lessened and even abolished. Secondly, hypothermia, which is classically required for this type of surgery, may be significantly reduced. This translates in a shorter cardiopulmonary bypass (CPB) time, less coagulation, respiratory and kidney problems (all linked to CPB duration).

According to another aspect of the present invention, there is provided an introducer system including a medical device carrier onto which a graft assembly as herein disclosed is fitted, the graft assembly being in a radially compressed state on the device carrier; and a sheath fitted over the graft assembly, wherein at least a portion of the sheath overlying the graft assembly is transparent or translucent.

As the graft assembly is intended to be deployed at an open (severed) end of the descending aorta, opened by sternotomy, the introducer system in combination with the graft assembly permits deployment without the need for X-rays or other imaging radiation during the process.

Advantageously, the system includes a proximal end and a distal end, an introducer tip being present at the distal end; the graft assembly being carried on the device carrier with the stented first graft portion thereof disposed facing the distal end and the non-stented second portion being disposed proximally thereto. The transparent or translucent sheath allows the surgeon to locate the unstented cuff at the location of the cut in the descending aorta, such that the stented part of the assembly fits in the aorta substantially in line with the severed end of the aorta. In this manner, not only is the aorta fully supported by the stented graft portion but optimal use of the cuff is also assured.

Advantageously, the sheath is splittable.

According to another aspect of the present invention, there is provided a method of treating aortic disease including the steps of:

opening a patient's aorta at or proximate the aortic arch;

cutting transversally the descending aorta proximate the aortic arch;

disposing into the descending aorta a unitary tubular graft element having a length, a first end, a second end and an axis; a plurality of stent elements extending along a majority of the length of the tubular graft element from the first end thereof, to provide a stented first portion of the tubular graft element; the tubular element from an end of the first stented portion to the second end being free of stents and forming a non-stented second portion of the tubular graft element; wherein the second portion is a minor portion of the length of the tubular graft element; the second portion having a circumference at least large as a circumference of the first portion;

everting the second portion over the transversally severed aorta wall, thereby to form a cuff to the tubular graft element, the cuff overlapping the aorta wall and the first portion of the tubular graft element; and suturing a second graft element to the tubular graft element, wherein the second graft element is formed to fit to the aortic arch of a patient.

Advantageously, the cuff is sutured to the aorta wall. In the preferred embodiment, the cuff is sutured to a non-everted part of the tubular graft through the aorta wall. By suturing the graft section to itself there can be assured a strong suture tie, as well as a good connection to the vessel wall.

Preferably, the method includes the step of disposing the stent graft assembly into the descending aorta by means of an introducer assembly having a transparent or translucent sheath overlying the stent graft. In this manner, therefore, the stent graft assembly can be disposed into the descending aorta without X-ray or other imaging procedures.

Other aspects and advantages of the teachings herein are described below in connection with the preferred embodiments disclosed herein.

BRIEF DESCRIPTION OF THE DRAWING

Embodiments of the present invention are described below, by way of example only, with reference to the accompanying drawings, in which.

DETAILED DESCRIPTION

It is to be understood that the drawings are schematic only and not to scale. Often, only the principal components relevant to the teachings herein are shown in the drawings, for the sake of clarity.

The embodiments described below relate to a graft assembly for use as a prosthetic replacement to a diseased aorta and specifically the aortic arch and descending aorta. The assembly may also replace at least a portion of the ascending aorta.

The graft assembly is formed in two sections or elements which are connected together, typically by suturing, during the surgical procedure. The first part of the assembly is a graft element designed and intended to fit into the descending aorta and to terminate just above a cut or severe line made in the descending aorta. This graft element and the introducer assembly therefor are described in detail below. The second part of the assembly is an arch element intended to replace at least the aortic arch and often also at least a part of the ascending aorta. It is herein referred to as a graft element although it is to be understood that the term "graft" is used in a broad sense. Separating the graft into two parts in this manner, it has been found, can substantially facilitate and improve the surgical procedure, in that a second part specific to the patient's anatomy and diseased condition can be provided. Moreover, the placement and attachment of this part to the heart and branch arteries is notably more straightforward, without needing also to account for a portion of the assembly already deployed in the descending aorta, that is prior coupled to the vessel wall or still held in or by an introducer assembly. The first part, that is the element which is deployed in the descending aorta, can be made as a substantially standard component and can be deployed in a first phase of the surgical procedure. Its deployment can be completed before the aortic arch section is fitted and distal perfusion re-established quickly. Only once both graft element are connected to their associated vessels do they need to be connected to one another. The inventors have found that with this structure it is possible to carry out a prosthetic replacement of this nature within 20 to 30 minutes, that is significantly faster than existing procedures. Reducing surgical time and optimising the nature and deployment of the prosthetic device, as is possible with the teachings herein, can significantly improve the chances of a successful outcome and also reduce the risk of morbidity and mortality.

FIGS. 1 to 4 depict in generalised terms the medical condition addressed herein and the steps of the disclosed surgical procedure to treat the diseased vessels.

The term "diseased" is used herein to refer to a vessel which is in any way in need of repair. This may be due to vessel damage, to weakening of the vessel wall, to disease in the wall tissue, and so on. The skilled person will be aware of the range of medical conditions which could benefit with a treatment of the type discussed herein.

Figure 1:
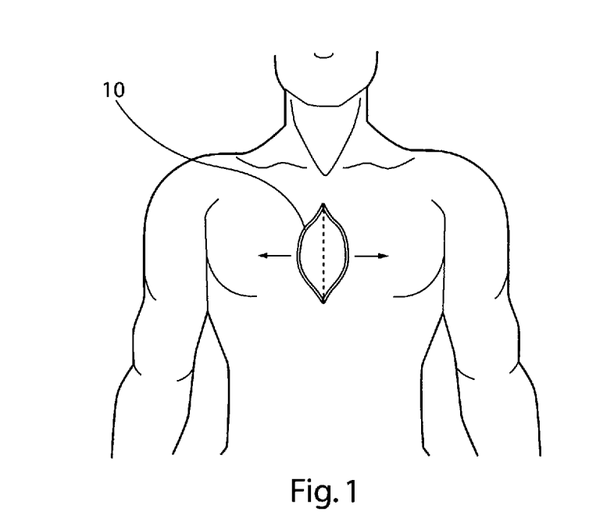
FIG. 1 is a sketch of a patient showing the point of entry via the patient's sternum.

Referring first to FIG. 1, this depicts the point of entry into a patient for carrying out the procedure taught herein, namely by a patient sternotomy 10, in which the patient's sternum is cut longitudinally and the patient's chest then opened laterally to gain access to the aorta. No other apertures into the patient are required, specifically a second access point in the zone of the descending aorta.

Figure 2:
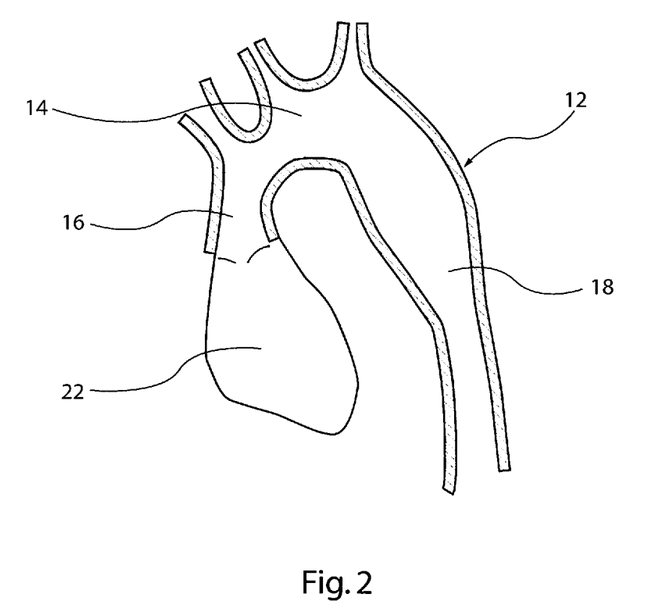
FIG. 2 is a sketch depicting an example of aortic disease intended to be treated by the apparatus and method taught herein.
Figure 3:
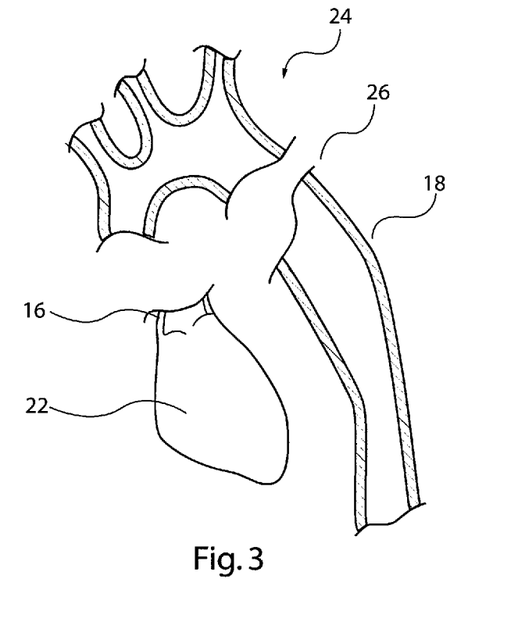
FIG. 3 is a sketch depicting the removal of a diseased aortic arch section of a patient.

FIG. 2 shows schematically an example of a diseased aorta 12, in which the entire aortic arch 14, at least a section of the ascending aorta 16, and at least a section of the descending aorta 18 have diseased arterial walls which require replacement or support. FIG. 3 depicts the surgical step necessary in this instance, namely transversally cutting (severing) the descending aorta 18, in this example proximate the left subclavian artery, the aortic arch together with at least a part of the branch openings into the right subclavian artery and the carotid arteries, the latter three being cut beyond the diseased portions thereof. In addition, the ascending aorta 16 is also transversally cut, proximate the heart 22. Following these cuts, the major part 24 of the diseased aorta 12 can be removed, while the diseased descending aorta 18 is left in place, thereby saving the need to make a larger opening into the patient. The procedure requires, as is known in the art, the use of a mechanical heart pump and bypass tubing for providing continued blood flow to the patient's vital organs, as well as the slowing or temporary stoppage of the heart, usually by cooling. As these surgical steps are known in the art, they are not described in detail herein.

Figure 4:
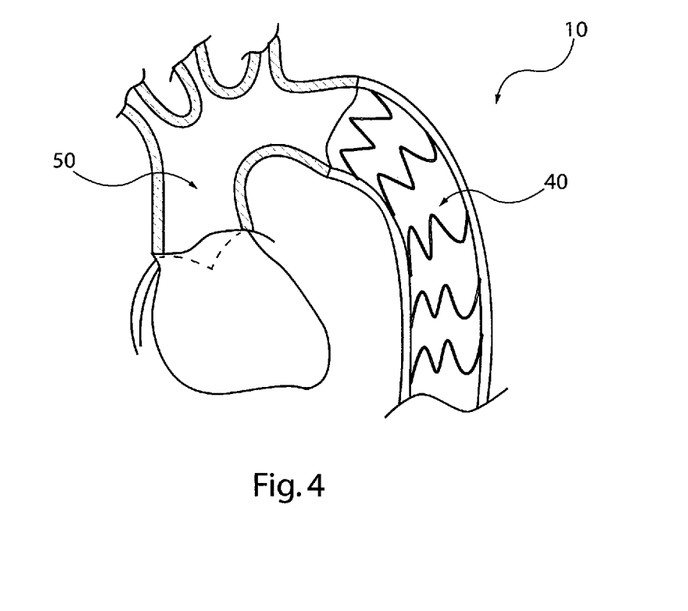
FIG. 4 is a sketch depicting the deployment of a two-part graft assembly as taught herein.

FIG. 4 depicts schematically the aorta 10 with the prosthetic graft according to the teachings herein fully deployed. The descending graft element 40 is shown fitted into the descending aorta 18, and in practice secured thereto, while an aortic arch graft element 50 is attached to the descending graft element 40 and fitted in replacement of the patient's own aortic arch. As the entire procedure can be carried out via a sternotomy, surgical trauma to the patient, surgery times and temporary loss of distal perfusion can be significantly reduced. Further details of the resultant structure and deployment process are described below.

Figure 5:
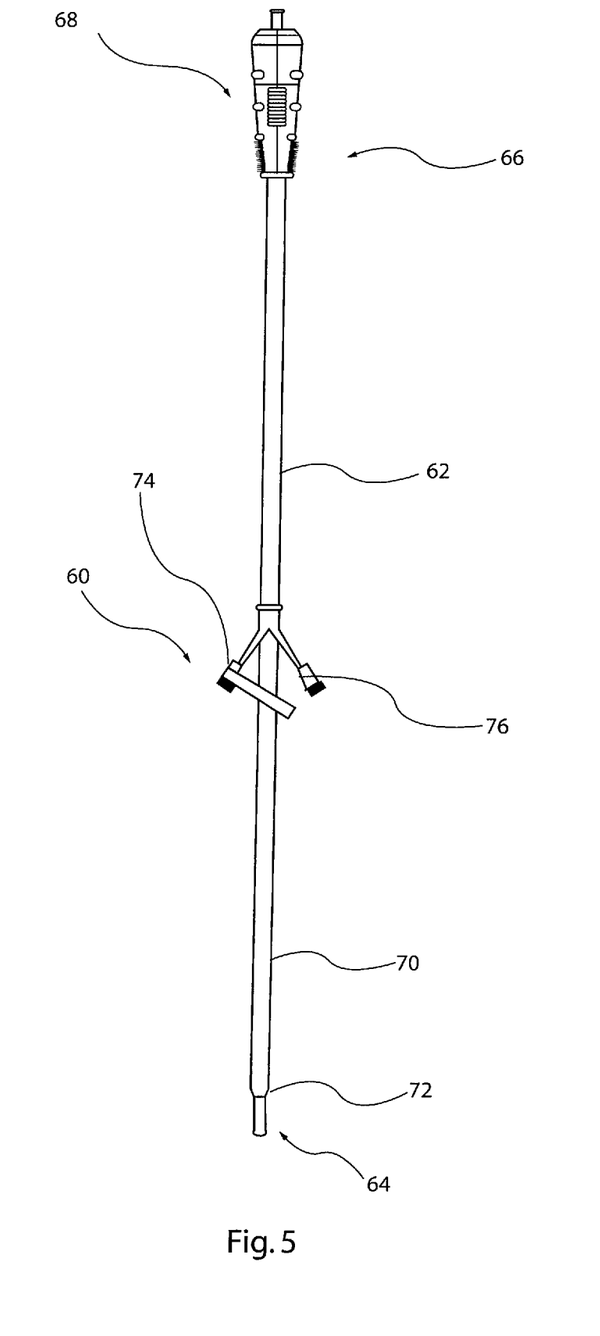
FIG. 5 is a schematic diagram of a preferred embodiment of introducer assembly.

Referring now to FIG. 5, this shows in schematic form the preferred embodiment of introducer assembly 60. The assembly 60 shown in FIG. 5 is in its pre-use condition. It includes an outer sheath 70 which holds the internal components, including a device carrier 62. A blunt tip 64, typically a dilator tip, can be seen extending beyond a distal extremity 72 of the sheath 70. At the other, proximal, end 66, the assembly is provided with a handle element 68 for operating the various parts of the introducer assembly 60. The handle 68 may be of a type well known in the art and is therefore not described in detail herein as its components and their operation will be familiar to the skilled person.

The blunt tip 64 allows the assembly 60 to be used without a wire guide, and this may be advantageous in many procedures. However, it is preferred that the device carrier 62 is in the form of a cannula with a lumen passing all the way along the assembly 60 and through the blunt tip, thereby allowing the use of a wire guide. A wire guide may be advantageous in some medical procedures, for instance when the lumen of the descending aorta is difficult to access, for instance in when the aorta has dissected. The carrier is preferably made of a stiff material, Nitinol being a preferred option.

In the preferred embodiment, the sheath 70 is a 24Fr (8.0 mm inner diameter) sheath, having an outer diameter of 26Fr (8.8 mm). The sheath could be taken down to 20Fr inner diameter without compromising deployment force. The sheath 70 is preferably clear, that is transparent or translucent, for the entire of its length, which enables procedure to be carried out without X-rays, that is under visual control. The sheath may typically have a length of 30 to 50 centimetres, dependent upon the length of the stent graft held on the introducer assembly.

The sheath 70 is preferably a splittable or peelable sheath, again of a type known in the art, so that this may be removed to release the implantable medical device 40 without having to slide the sheath 70 over the medical device 40. This assists in ensuring that the cuff portion 52 is not squashed or folded longitudinally during the deployment process. For this purpose, the sheath may include a pair of pull tabs 74, 76

At least a distal section of the sheath 70, which overlies the graft element 40, is made of a transparent or translucent material, such that the physician can see the graft 40 when the latter is disposed in the introducer assembly 60. This, as will become apparent below, enables the physician to locate and deploy the graft element 40 without the need for x-rays or other imaging devices. The sheath 70 can be made of any suitable material, most preferably polytetrafluoroethylene (Teflon). It is preferably of a single material and of a single layer.

Although only the distal end of the sheath 70 could be of transparent or translucent material, in preferred embodiments the entire length of the sheath 70 is made of such a material and is therefore of unitary construction.

Figure 6:
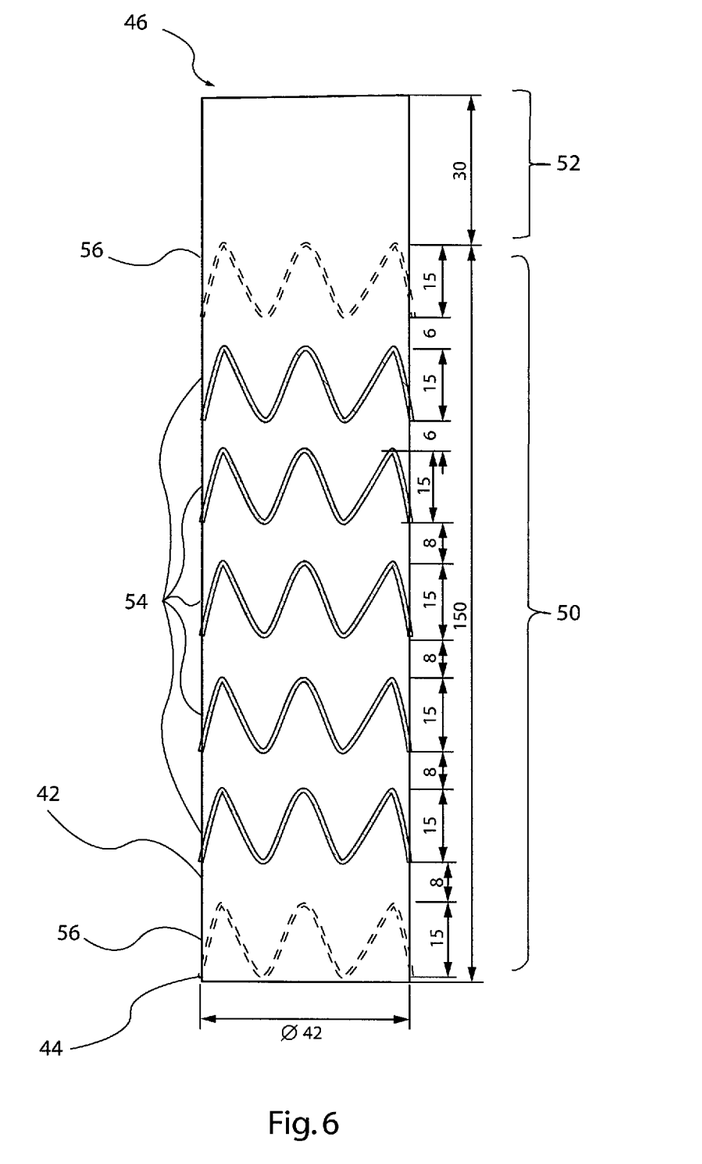
FIG. 6 is a side elevational view of a preferred embodiment of graft assembly for deployment in the descending aorta.

Referring now to FIG. 6, this shows a preferred embodiment of graft section forming part of a multi-section prosthetic assembly of the type disclosed herein. This graft section 40, which may be described as a descending aorta graft section, includes a tubular graft element 42 having a distal end 44 and a proximal end 46. The tubular graft element 42 is, in this embodiment, cylindrical, that is has the same open diameter throughout its length. In the embodiment shown, the graft tube 42 has an open diameter of around 42 mm, although in practice it may typically have an open diameter of anything between 30-46 mm, more typically of 32 to 42 mm. The skilled person will appreciate that this diameter is dependent on the anatomy of the patient to be treated. Although the tubular graft element 42 is cylindrical in this embodiment, it need not be so. In other embodiments it could have a varying diameter along its length, for instance to have a distal diameter that is smaller than the proximal diameter.

The tubular graft element 42 may be made of any conventional blood impervious material such as polyethylene terephthalate, polytetrafluoroethylene, polyester, these being just examples.

The graft section 40 can be considered to be formed of two portions, the first portion 50 being a stented portion, while the second portion 52 is unstented (that is, stent free).

The stented portion 50 includes a plurality of stents 54, preferably formed of Nitinol or stainless steel, which are secured to the graft tubing in any conventional manner. The stents 54 are disposed on the outside of the graft tubing, although they may be disposed internally of the graft tubing or in a combination of the two. In the example shown in FIG. 6, at the two extremities of the stented portion 50 there are also provided end stents 56, which are fitted to the inside of the graft tubing 44. These end stents may be fitted to the outside of the graft tubing in some embodiments.

The end stents 56 are preferably provided with radiopaque markers, which may be of gold or other suitable material. Radiopaque markers are well known in the art so as not described in further detail herein.

In this embodiment, all the stents 54, 56 have a zigzag annular shape with substantially straight stent struts connected together at distal and proximal apices. The stents 54, 56 are separate rings spaced from one another in the longitudinal direction of the graft tubing 42, as shown in FIG. 6. In one example, each stent 54, 56 may have a height of around 15 mm and the stents may be spaced from one another along the graft tubing 42 by around 8 mm. In this embodiment, the stented section 50 has a length in the region of 150 mm. It will be appreciated, though, that the dimensions of the stents, their heights, spacing, and the length of the stented section 50 may vary from one practical embodiment to another. There may equally be different numbers of stents from the seven stents depicted in FIG. 6.

The unstented section 52 extends from an end of the stented section 50 and in this example for a length of around 30 mm. The unstented section may typically have a length of anything from around 25-35 mm. In the preferred embodiment shown in FIG. 6, the unstented section constitutes around 17% of the length of the graft sleeve 42. It forms a minor part of the length of the graft sleeve 42 and therefore also of the descending graft element 40.

In a practical embodiment, the graft 44 has a total length of between 100 to 200 mm of which the unstented section is around 30 mm.

While in the embodiment shown in FIG. 6 the graft tubing 44 is cylindrical so as to have the same open diameter throughout its length, other embodiments may have a tapering (frusto-conical) form, typically with the larger diameter end being at the unstented section 52. In other embodiments, the unstented portion 52 may be cylindrical but have a larger open diameter than the stented portion 50, which may equally by cylindrical. In this embodiment, the unstented portion 52 would therefore be wider than the stented section 50, which, as will become apparent below, can facilitate the eversion of the unstented portion 52 over and outside the stented portion 50. Other non-cylindrical forms are equally contemplated.

The unstented portion 52 acts as a cuff to the prosthetic assembly, for fixing the descending graft element 40 to the descending aorta 18 and as a fixation point for the aortic arch prosthetic element.

Figure 7:
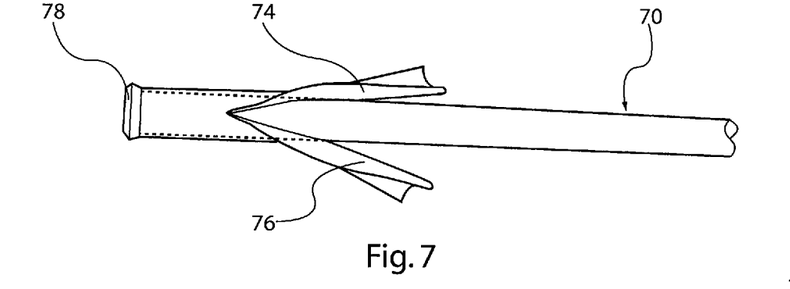
FIG. 7 is a side elevational view of a transparent sheath of the preferred embodiment of introducer assembly.
Figure 8:
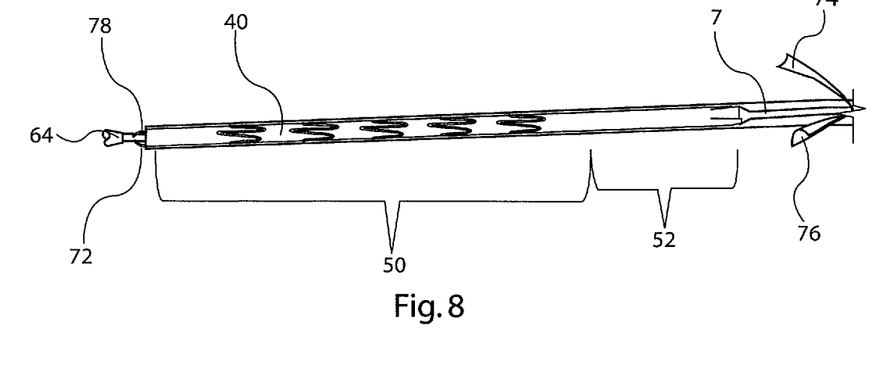
FIG. 8 is a side elevational view of the distal end of an embodiment of introducer assembly with the stent graft held therewithin.

Referring now to FIGS. 7 and 8, these are photographs showing, respectively, the see-through sheath 70 and the distal end of the introducer assembly 60 with the descending aorta graft section fitted therein.

In the photograph of FIG. 7, the proximal end of the sheath 70 is shown. As can be seen, the sheath 70 is, in this example, made of a translucent material and includes a pair of pull tabs 74, 76 which are diametrically opposed. The sheath 70 is split between the pull tabs 74, 76, such that when they are pulled apart the split propagates towards the everted proximal sheath end 78 and then up the length of the sheath 70 to its distal end 72 adjacent the tip 64. The splittable sheath 70 has a structural form known in the art.

Referring to FIG. 8, as can be seen, the graft element 40 is disposed such that the stented section 50 is positioned distally and the unstented section 52 is disposed proximally on the introducer assembly 60. In practice, the unstented section 52 of the graft element may be placed in abutment with a pusher member of the carrier 62 (not shown). In other embodiments, in place of or in addition to a pushed member, the graft element 40 may be tied to the carrier by means of one or more restraining wires, such as the wires 78 shown extending to the tip 64 in FIG. 8.

Figure 9:
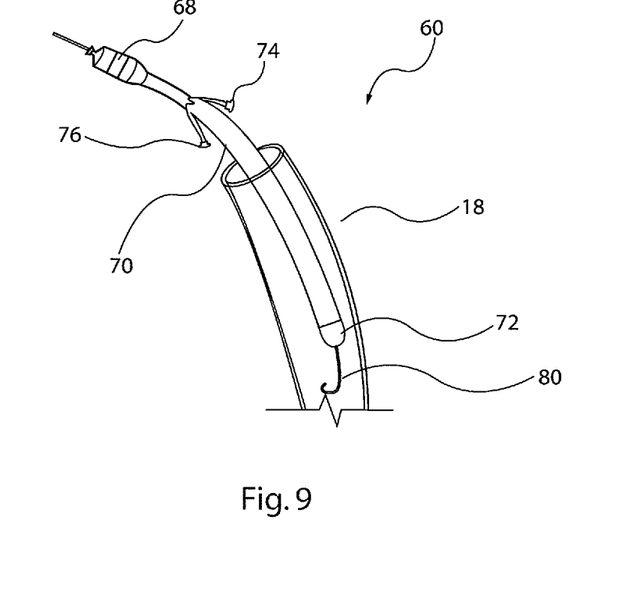
FIGS. 9 and 10 are schematic diagrams of the distal end of the introducer assembly of FIG. 8 positioned into the descending aorta of a patient.
Figure 10:
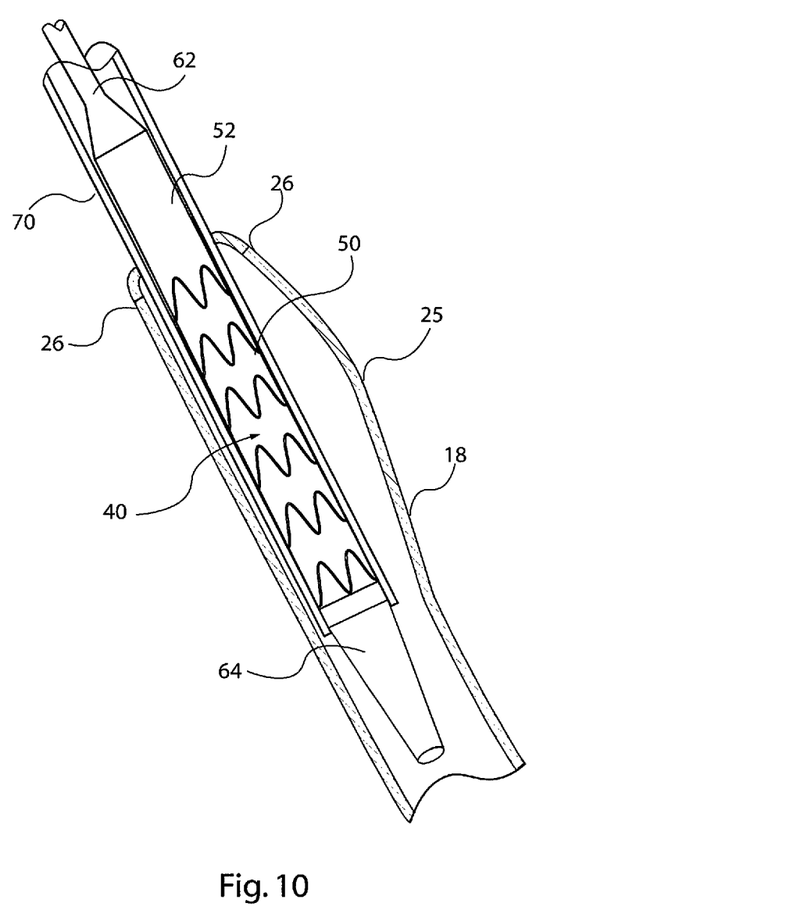

Referring next to FIGS. 9 and 10, these depict the positioning of the introducer assembly 60 into the descending aorta 18. The distal end 72 of the introducer assembly 60 is positioned into the severed end 26 of the descending aorta 18 and in practice, as is described in detail below, such that the unstented section 52 of the graft 40 in the introducer assembly 60 remains above the severed end 26.

As will be apparent from FIGS. 9 and 10, access to the descending aorta 18 is via the sternotomy 10, which as a result avoids the need to make a second access opening into the patient By way of example only, the descending aorta 18 is shown having a weakened zone 25, which may be an aneurysm, a dissection or other defect.

The distal end 72 of the introducer assembly 60 is located into the descending aorta 18 up to the end of the stented portion of 50 the graft element 40, such that the stented portion 50 resides entirely within the descending aorta. This portion 50 is chosen to have a length sufficient to bypass the entirety of the weakened zone 25. The unstented (stent free) portion 52 of the graft element 40, that is the cuff, is kept outside of the descending aorta and specifically above the cut line 26, as viewed in FIGS. 9 and 10. This is achievable for the reason that the sheath 70 is transparent or translucent, enabling the physician to see precisely and align the graft element 40 in the descending aorta 18.

In FIG. 9 the procedure is shown being performed over a guide wire 80. While this is strictly not necessary, there are some medical conditions in which this may be advantageous, such as when it is difficult to ensure proper placement of the introducer 60 into the main lumen of the descending aorta.

This may occur, for example, when the aorta 18 is dissected. An over-the-wire 80 procedure may, though, only be necessary in a few instances.

It should also be appreciated that since the procedure is carried out from the open sternotomy and removed aortic arch, the introducer assembly 60 can be relatively short, thereby making it easy for the physician to handle the assembly and position the graft element 40 accurately within the descending aorta 18.

Figure 11:
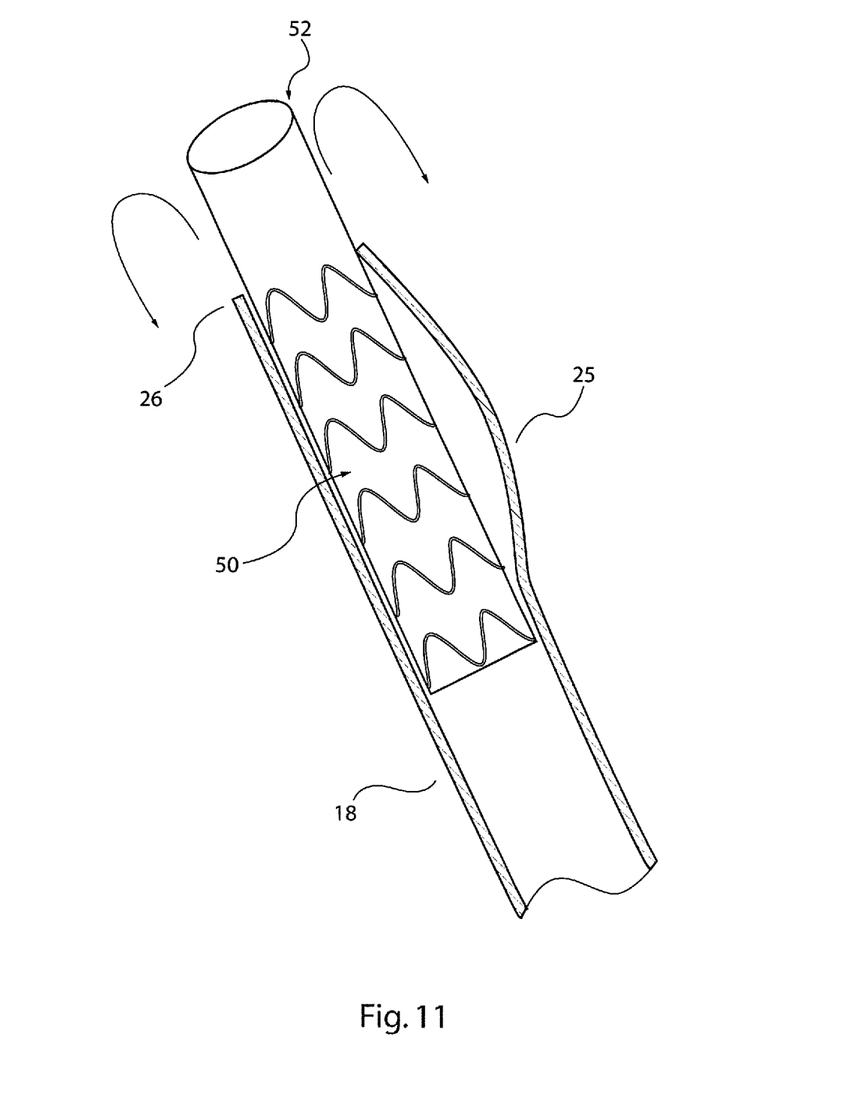
FIG. 11 is a schematic diagram of the descending graft element once released from the introducer system.

Referring now to FIG. 11, this is a view similar to FIGS. 9 and 10, in which the graft section 40 has been released from the introducer assembly 60, the latter having been removed from the descending aorta 18. As can be seen, the stented portion 50 expands to the vessel wall, to be secured thereto, and acts as a prosthetic bypass to the section of the descending aorta 18 which it covers. The stented section 50 may be provided with one or more barbs and one or both ends thereof for anchoring the graft element 40 to the descending aorta 18.

On the other hand, the cuff 52 can be seen extending out of the descending aorta 18, above the cut line 26. The cuff 52 is folded back, that is everted, in the direction depicted by the arrows in FIG. 10, so as to overly a part of the descending aorta 18 and also a part of the stented portion 50 of the graft element 40. The cuff 52 may be trimmed to size by the physician.

Figure 12:
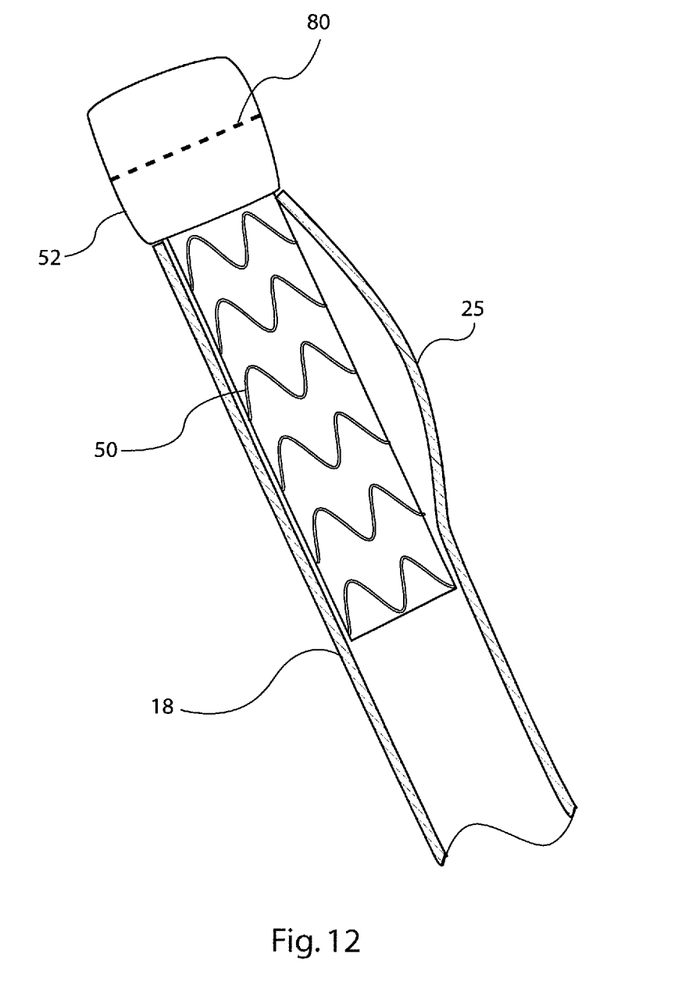
FIG. 12 is a schematic diagram of the descending graft element with the cuff everted over the descending aorta wall.

Referring now to FIG. 12, this shows the configuration with the cuff 52 everted in this manner. The cuff 52, and as a result the entire graft element 40, is fixed to the descending aorta 18 by means of at least one suture. In the example shown in FIG. 12, there is shown a suture line 80 extending circumferentially around the cuff. There may be provided a plurality of suture lines or sutures in other arrangements for fixing the cuff 52 to the descending aorta 18.

It is preferable that the sutures pass all the way through the cuff, the vessel wall and the graft material of the stented portion 50, so as to provide a very secure attachment of the graft element 40 to the descending aorta 18. It is not excluded, however, that in some embodiments the sutures 80 may be passed solely through the cuff 52 and the walls of the descending aorta 18.

In addition to providing a secure attachment, the everted cuff 52 secures the top of the descending aorta 18, which can be particularly advantageous when the latter is weakened.

The stent graft 40 is deployed antegrade during circulatory arrest. The use of a transparent or translucent sheath allows the physician to position the unstented cuff 52 at the level of the arch transection for performing distal anastomosis.

The descending aorta graft section can effect an endovascular repair of the thoracic aorta, for instance to cover a dissection and thrombosing false lumen.

Figure 13:
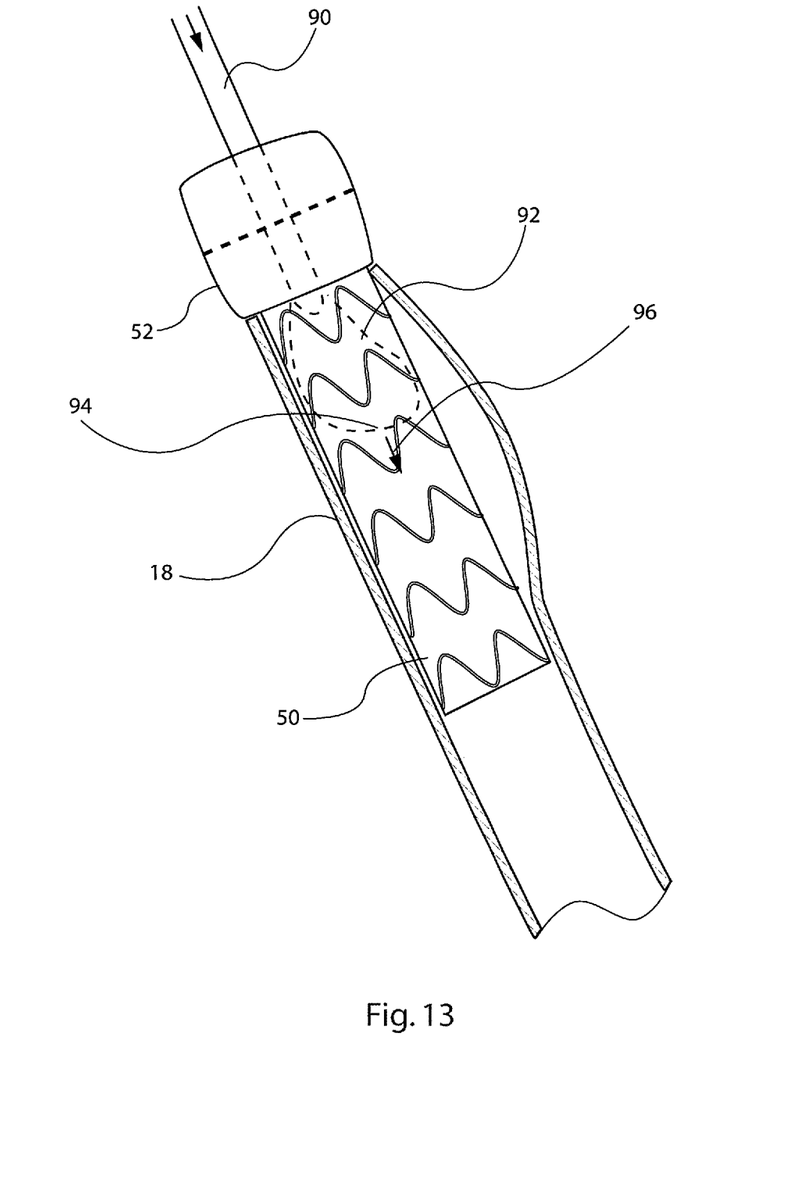
FIG. 13 is a schematic diagram of the descending graft element with the descending stent graft section fitted and distal perfusion re-established.

Referring now to FIG. 13, this shows the graft section 40 in position in the descending aorta following a distal anastomosis. Once deployed, an endotracheal tube 90 is inserted into the lumen of the graft section 40 to re-establish distal perfusion during circular arrest and arch reconstruction by means of the aortic arch section of the hybrid graft assembly. The endotracheal tube includes an expandable bulbous head 92 which presses against the inner graft wall of the section 40, thereby to seal thereto. A narrow exit aperture 94 in the expandable head 92 allows for flow of blood into the descending aorta, as well as expansion pressure to the head 92, thereby establishing distal perfusion.

Distal perfusion through the endotracheal tube is maintained throughout the distal anastomosis.

The provision of two separate elements to the hybrid assembly also means that an aortic arch section can be provided specifically for that patient's condition and anatomy, which can significantly speed up the surgical process and provide a prosthetic replacement much better suited to that patient. Increased speed and the possibility of re-establishing perfusion into the descending aorta during the procedure can significantly reduce or eliminate the risk of medical complications caused by the procedure.

Specifically, providing the possibility to perfuse within the stent-graft during circulatory arrest minimises the risk of distal ischemia, including to the spinal cord, thus decreasing or eliminating the risk of paraplegia. The preferred embodiments provide the following additional advantages:

(i) a short and easy pusher rod deployment system;
(ii) a transparent or translucent sheath which allows controlled and precise graft deployment;
(iii) a proximal un-stented graft portion which can be easily tailored to the aortic arch wall;
(iv) since the graft is terminated at the level of the transected arch, an endotracheal tube may be inserted and inflated within the hybrid stent allowing for distal body perfusion. This may be done before and during the distal anastomosis; These advantages have significant clinical impact. The easy and reliable deployment system may be adapted to many clinical situations in addition to type A dissections, such as distal arch aneurysms and chronic dissection cases. The possibility to initiate distal perfusion has significant benefits. First, this ensures distal body perfusion including spinal cord perfusion. Paraplegia risk can be significantly lessened and even abolished. Secondly, hypothermia, which is classically required for this type of surgery, may be significantly reduced. This translates in a shorter cardiopulmonary bypass (CPB) time, less coagulation, respiratory and kidney problems (all linked to CPB duration).

Figure 14:
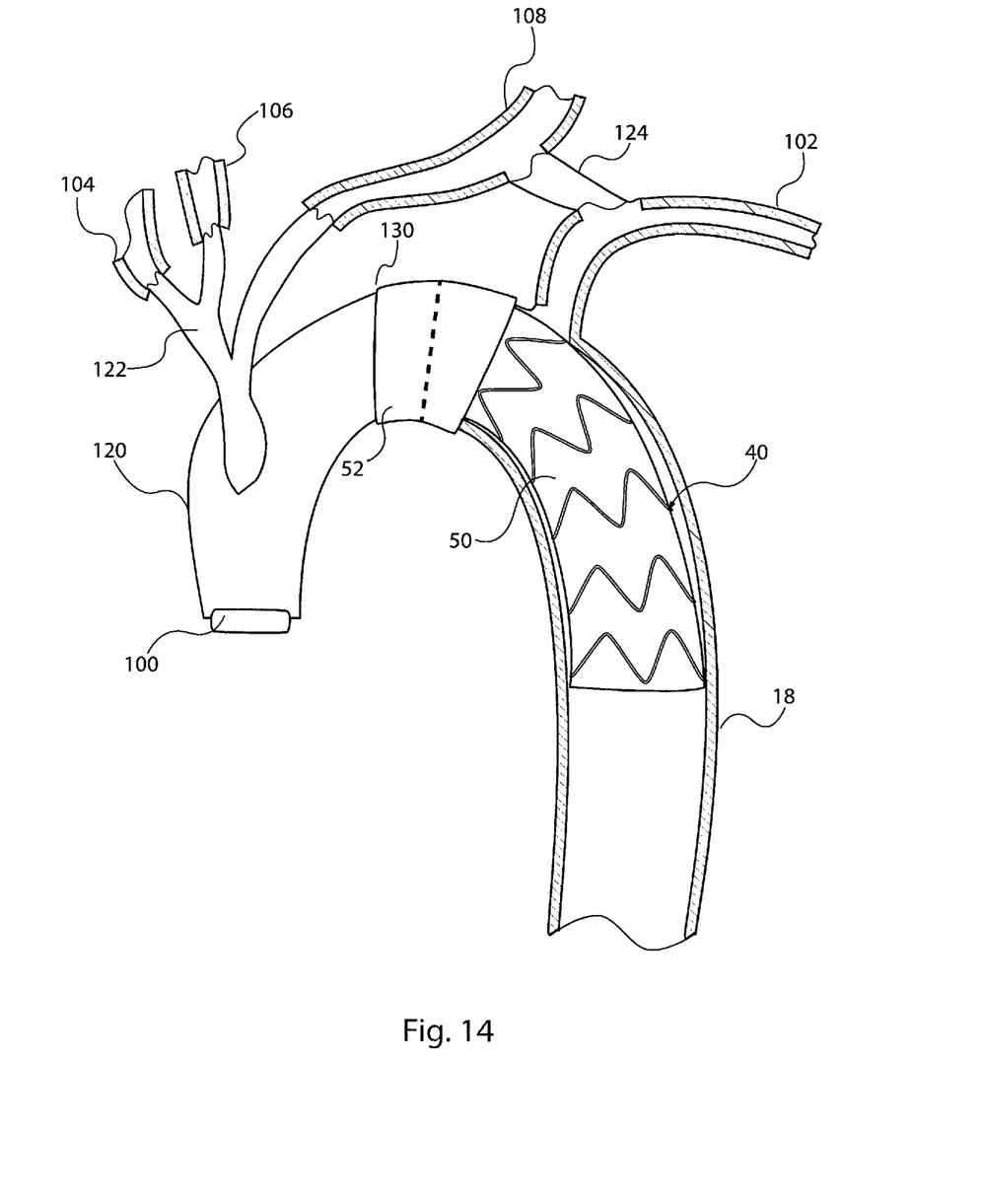
FIG. 14 is a schematic diagram of an embodiment of graft assembly shown fitted in a patient's aorta.

Referring now to FIG. 14, this shows an example of an entire graft prosthesis in accordance with the teachings herein, when in situ within a patient. For the sake of clarity, the patient's heart is not depicted in FIG. 12, the sketch terminating at the heart valve 100.

In this example, the descending aorta graft element 40 is fitted in the manner shown in FIG. 12 and in this example extending beyond the left subclavian artery 102. It will be appreciated that the entrance to the left subclavian artery will be occluded by the stented graft portion 50, in this example necessary as a result of disease of that portion of the aorta. The cuff 52 is everted and sutured in the manner explained above and connected to a second graft element 120 which replaces the aortic arch and the ascending aorta, in this example until the heart valve 100, which may the original heart valve or a prosthetic replacement. As can be seen, the second graft section 120 includes a branch vessel 122 which leads to the right subclavian artery 104, the right carotid artery 106 and the left carotid artery 108. A bypass graft 124 connects from the left carotid artery to the left subclavian artery 102, thereby addressing the issue of the obstruction at the entry of the left subclavian artery 102 by the graft section 40.

The second graft section 120 is fixed to the first graft section 40 at the point at which it couples to the distal end of the cuff 52, that is at the point indicated at 130. It is typically sutured to and around the circumference of the cuff 52 so as to provide an integral structure.

Figure 15:
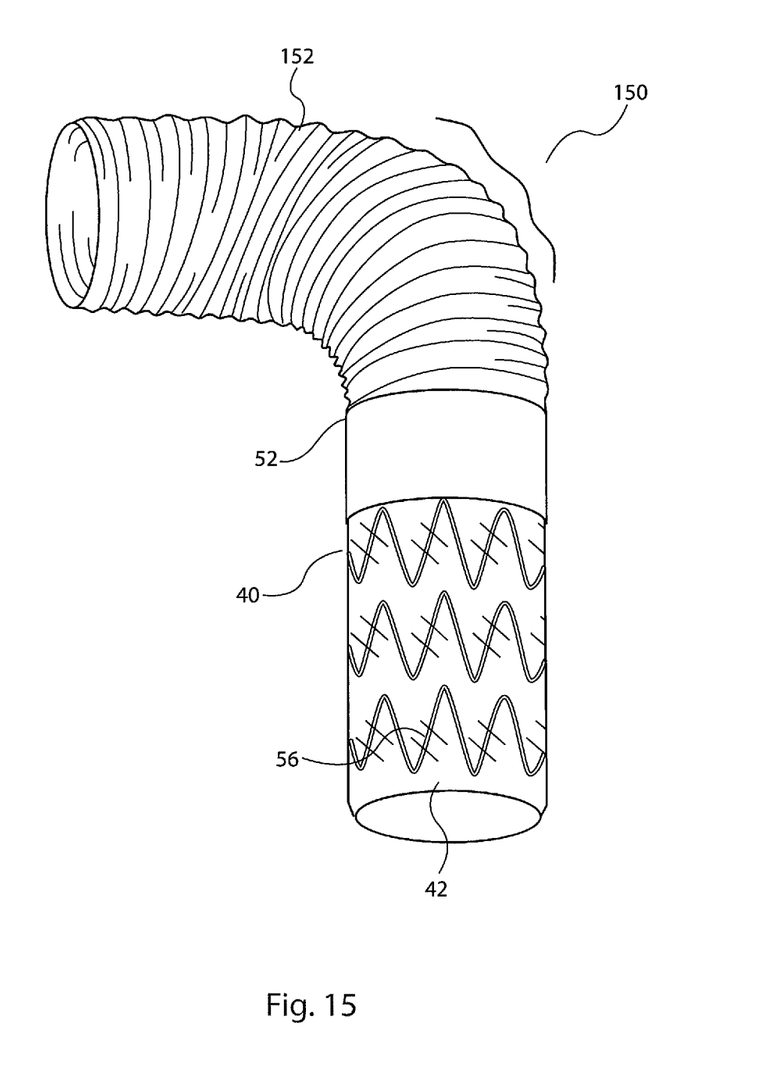
FIG. 15 is a diagram of a corrugated elephant trunk deployable by the system and method taught herein.

FIG. 15 shows another example of assembly 150, which includes an elephant trunk section 152 for replacement or for lining the aortic arch, and which is sutured to the descending aortic graft element 40 at the cuff 52. The elephant trunk section, which is a known medical device, can be sutured to the walls of the remaining aortic vessels and cut as appropriate to provide fluid passage to the arteries 104-108. An elephant trunk element of this type is typically used where there is less extensive damage to the aorta.

As the graft assembly is provided in two sections, it is possible to select an aortic arch graft element which is specifically designed or suited to the medical condition to be treated and the patient's anatomy, therefore of optimal design for that purpose. On the other hand, the graft element 40 for the descending aorta can be provided as a separate component and which is of generally of standard form and size. As the two elements 40, 120/150 of the assembly can be attached separately to their respective aortic vessels and then coupled together only once so fitted, it has been found that overall the surgical procedure is much faster and provides a better prosthetic replacement than prior art methods. In other words, it is possible to choose the best technical option for each particular patient. The inventors have found that it is possible to carry out a surgical procedure with the assembly taught herein in half an hour or less, which is much faster than existing procedures with existing devices. In any event early re-establishment of distal perfusion is a significant benefit.

The stents used in the stented portion 50 of the graft element 40 may be self-expanding stents or balloon expandable stents. In the case of balloon expandable stents, the introducer assembly 60 may be provided with a deployment balloon as part of the device carrier, in a manner which will be apparent to the person skilled in the art.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

What is claimed is:

1. A graft assembly comprising:
a unitary tubular graft element having a length, a first end, a second end and an axis;
a plurality of stent elements extending along a majority of the length of the tubular graft element from the first end thereof, to provide a stented first portion of the tubular graft element:
the tubular graft element from an end of the first stented portion to the second end of the graft element being free of stents and forming a non-stented second portion at the second end of the tubular graft element;
wherein the non-stented second portion is a minor portion of the length of the tubular graft element;
the second portion having a circumference at least as large as a circumference of the first portion so that the second end of the tubular graft element is eversible over the first portion to form a coaxially overlapping cuff to the tubular graft.

2. A graft assembly according to claim 1, wherein the second portion of the tubular graft element has a length at least one of 20 to 40 millimetres.

3. A graft assembly according to claim 1, wherein the first portion of the tubular graft element has a length of 10 to 20 centimetres.

4. A graft assembly according to claim 1, wherein the tubular graft element has a single lumen.

5. A graft assembly according to claim 1, wherein the tubular graft element has a substantially cylindrical form.

6. A graft assembly according to claim 1, wherein the first and second portions of the tubular graft element have substantially the same open diameter.

7. A graft assembly according to claim 1, for use in the treatment of the descending aorta, wherein the second end of the tubular graft element is eversible over a transversally severed aorta wall.

8. A graft assembly according to claim 1, including a second graft section configured to be sutured to the tubular graft element, wherein the second graft section is formed to fit to the aortic arch of a patient.

9. An introducer system comprising:
a medical device carrier, a graft assembly fitted on the device carrier in a radially compressed state, and a sheath fitted over the graft assembly;
wherein the graft assembly comprises a unitary tubular graft element having a length, a first end, a second end and an axis;
a plurality of stent elements extending along a majority of the length of the tubular graft element from the first end thereof, to provide a stented first portion of the tubular graft element;
the tubular graft element from an end of the first stented portion to the second end of the graft element being free of stents and forming a non-stented second portion at the second end of the tubular graft element;
wherein the non-stented second portion is a minor portion of the length of the tubular graft element;
the second portion having a circumference at least as large as a circumference of the first portion so that the second end of the tubular graft element is eversible over the first portion to form a coaxially overlapping cuff to the tubular graft; and
wherein at least a portion of the sheath overlying the graft assembly is transparent or translucent.

10. An introducer system according to claim 9, wherein the medical device carrier includes a proximal end and a distal end, an introducer tip being present at the distal end; the graft assembly being carried on the device carrier with the stented first graft portion thereof disposed facing the distal end and the non-stented second portion being disposed proximally thereto.

11. An introducer system according to claim 9, wherein the entire length of the sheath is transparent or translucent.

12. An introducer system according to claim 10, wherein the sheath is made from a transparent or translucent plastics material.

13. An introducer system according to claim 12, wherein the sheath is made from polytetrafluoroethylene.

14. An introducer system according to claim 9, wherein the sheath is splittable.

15. An introducer system according to claim 13, wherein the second portion of the tubular graft element has a length at least one of 20 to 40 millimetres.

16. An introducer system according to claim 15, wherein the first portion of the tubular graft element has a length of 10 to 20 centimetres.

17. An introducer system according to claim 9, wherein the tubular graft element has a single lumen.

18. An introducer system according to claim 9, wherein the first and second portions of the tubular graft element have substantially the same open diameter.

19. An introducer system according to claim 9, wherein the tubular graft element is formed of a fabric of polyethylene terephthalate, polytetrafluoroethylene (PTFE) or polyester.

20. A method of treating aortic disease including the steps of:
opening a patient's aorta at or proximate the aortic arch;
cutting transversally the descending aorta proximate the aortic arch;
disposing into the descending aorta a unitary tubular graft element having:
a length, a first end, a second end and an axis;
a plurality of stent elements extending along a majority of the length of the tubular graft element from the first end thereof, to provide a stented first portion of the tubular graft element;
the tubular graft element from an end of the first stented portion to the second end of the graft element being free of stents and forming a non-stented second portion at the second end of the tubular graft element;
wherein the non-stented second portion is a minor portion of the length of the tubular graft element;
the second portion having a circumference at least as large as a circumference of the first portion;
everting the second end of the tubular graft element over the transversally severed aorta wall, thereby to form a cuff to the tubular graft element, the cuff overlapping the aorta wall and the first portion of the tubular graft element; and
suturing a second graft element to the tubular graft element, wherein the second graft element is formed to fit to the aortic arch of a patient.

* * * * *